United States Patent [19]
Keller

[11] Patent Number: 5,738,517
[45] Date of Patent: Apr. 14, 1998

[54] APPARATUS AND METHOD OF FIXED REFERENCE EXAMINATION OF DENTAL PATIENTS

[76] Inventor: Duane C. Keller, 8930 Eden Ave., St. Louis, Mo. 63123

[21] Appl. No.: 546,922

[22] Filed: Oct. 23, 1995

[51] Int. Cl.$^6$ .................................................. A61C 19/04
[52] U.S. Cl. ........................................................ 433/73
[58] Field of Search .............................. 433/73; 128/845; 606/130

[56] References Cited

U.S. PATENT DOCUMENTS

| | | | |
|---|---|---|---|
| 1,674,088 | 6/1928 | Bodine | 433/73 |
| 3,200,497 | 8/1965 | Goodfriend | 433/73 |
| 3,218,716 | 11/1965 | Stuart | 433/73 |
| 3,693,260 | 9/1972 | Hernandez | 433/56 |
| 4,096,637 | 6/1978 | Stade | 433/73 |
| 4,616,998 | 10/1986 | Wong | 433/73 |
| 4,695,252 | 9/1987 | Edwardson | 433/73 |
| 4,892,480 | 1/1990 | Levandoski | 433/73 |
| 5,176,515 | 1/1993 | Andrews | 433/73 |
| 5,207,688 | 5/1993 | Carol | 433/73 |

*Primary Examiner*—Cary E. O'Connor
*Attorney, Agent, or Firm*—Polster, Lieder, Woodruff & Lucchesi

[57] ABSTRACT

A patient evaluation reference determining apparatus of the present invention comprises a face bow which extends generally from one of the patient's ears forwardly along the patient's temples or across the patient's face, and back along the other side of the patient's head from the patient's temple to the patient's other ear. The face bow has a pair of ear pieces which are connected to the face bow and each piece is adapted to be inserted in one of the patient's ear openings or potions. The apparatus further includes a nose piece carried by the front portion of the face bow with the nose piece engaging the patient's nasion. Adjustable locking connection are provided at the interconnection of the ear pieces and the face bow and at the nose piece and the face bow. A bubble level is carried by the face bow. The ear pieces and the temples may be adjusted so as to position at least the portion of the face bow carrying the bubble level to be in a true horizontal position and locked in place relative to one another, as established by the bubble level. In this manner, the patient's head is aligned relative to a true horizontal, level plane such that when radiographic or photographic images of the patient's cranium and jaw structure are taken, it is ensured that the patient's head and cranium structure are positioned in a true horizontal reference plane. This enables practitioners to repeatedly position the patient's head and jaw in this true horizontal reference plane.

A method of radiographic examination is disclosed utilizing the above patient evaluation reference determining apparatus.

9 Claims, 1 Drawing Sheet

APPARATUS AND METHOD OF FIXED REFERENCE EXAMINATION OF DENTAL PATIENTS

BACKGROUND OF THE INVENTION

This invention relates to an improved apparatus and method for dental patient evaluation, and, more particularly, to a method and system for providing a constant reference of orthodontic and orthopedic evaluation of dental patients using true horizontal and vertical reference planes, as opposed to prior art evaluation methods which used anatomic reference planes which are arbitrarily determined based on different reference points of the patient's skull and facial features.

Conventionally, when a dentistry patent is examined, there are a number of diagnostic aspects or techniques which are used. For example, radiographs, photographs, clinical evaluation, study models and other diagnostic apparatus are used to facilitate the examination process. Each of these methods is studied independently and then the dentist must interpret the meanings of these independent diagnostic tools and combine them to determine the anatomic aspects of the patient being studied.

Oftentimes, one of the radiographs, a lateral head film, is used for prediction of the patient's growth, spatial analysis, and evaluation of the anatomical and skeletal structures of the head. Typically, an arbitrary reference plane is established by taking the inner aspect of the ear canal (as it appears on the radiograph) as one point on the reference plane and by using the lower aspect of the eye-orbit as the second aspect to establish the plane. This reference plane, was initiated by anthropologists so that skulls could be oriented in a similar manner, and the use of such an arbitrary reference is also used in the orthodontics field.

However, there are some inherent errors with the system. First, the patient's inner ear may demonstrate a variety of arbitrary points, usually an outer ring of the ear canal and an inner ring of the ear canal. There are also a right and left series of canals which are superimposed thus providing even more room interpretive error. There are also two eye-orbits and the practitioner must determine which appears to be the best one to use, or interpret the difference between the two and select a point which is the difference between the two projections. As the result of some of these differences, different practitioners utilizing the same methodology often times establish different reference planes which lead to different interpretations of the patient's anatomical and dental features.

Still further, models are conventionally mounted using the above described arbitrary references of similar methods. Ear holders are used to position a face bow in the outer ear canal and an approximated orbit or anterior measurement is measured on the anterior aspect of the face. The upper model is then correlated with this arbitrary reference plane and is positioned on an articulator, thus positioning the models relative to the arbitrary reference plane. Both the radiograph and the mounted model use an arbitrary plane which is not accurately reproducible is not the same reference plane and is thus subject to interpretive errors. If multiple examiners or practitioners review the same patient utilizing these arbitrary reference planes, there is no way to ensure that their interpretation and establishment of the reference plane is the same as, or even close to, the reference planes established by other evaluators. There has been a need for a method and system of cephalometric examination of dental patients which does not rely on interpretive structural features in arbitrary reference planes.

SUMMARY OF THE INVENTION

Among the several objects and features of the present invention may be noted the provision of a method of patient analysis and an evaluation system which utilizes true horizontal and vertical reference planes in place of an arbitrary plane established by indefinite anatomical and skeletal features;

The provision of such an cephalometric evaluation system and method which substantially eliminates the above-discussed interpretive errors and which provides practitioners with the ability to accurately reproduce the relationship such that other practitioners may readily duplicate the radiographic references.

The provision of such an evaluation system and method which allows radiographs and models to be oriented relative to the same reference planes, and The provision of such an evaluation system and method which allows photographs and other visual partial analysis systems to be oriented to the same reference plane as the radiographs and models.

A dental patient evaluation method and system of the present invention comprises a face bow extending generally from one of the patient's ears forwardly along the patient's temples, across the front of the patient's face, and along the other side of the patient's head to the patient's other ear. A pair of fixed or adjustable ear pieces is connected to the face bow with each ear piece being adapted to be inserted into a respective one of the patient's ear openings or potions. A nose piece is carried by the portion of the face bow extending across the front of the patient's face and the nose piece engages the. patient's nasion. The face bow has a level carded thereon for establishing a horizontal reference plane. Optionally, a bite fork support member may be carried by the face bow and extends down generally from the nose piece and carries a bite fork which is adapted inserted into the patient's mouth. The bite fork support member has another level carried thereon for establishing that with the face bow in a horizontal plane that the bite fork is supported in a vertical plane.

The method of the present invention comprises placing a face bow on the patient's head with the face bow having temple pieces extending along the sides of the patient's head and the face bow extends laterally across the front of the patient's face. Ear pieces extend down from each of the temple pieces and ear fingers are placed in the patient's ear openings or potions. A nose piece is brought into contact with the patient's nasion and a horizontal plane is established. Then, radiographs or photographs or impressions of the patient may be taken with the patient's head in this established horizontal plane.

Other objects and features and this invention will be in part apparent and in part pointed out hereinafter.

BRIEF DESCRIPTION OF THE DRAWINGS

Corresponding reference characters indicate corresponding parts there at the several views of the drawing.

DESCRIPTION OF THE EMBODIMENTS

Figure 1:
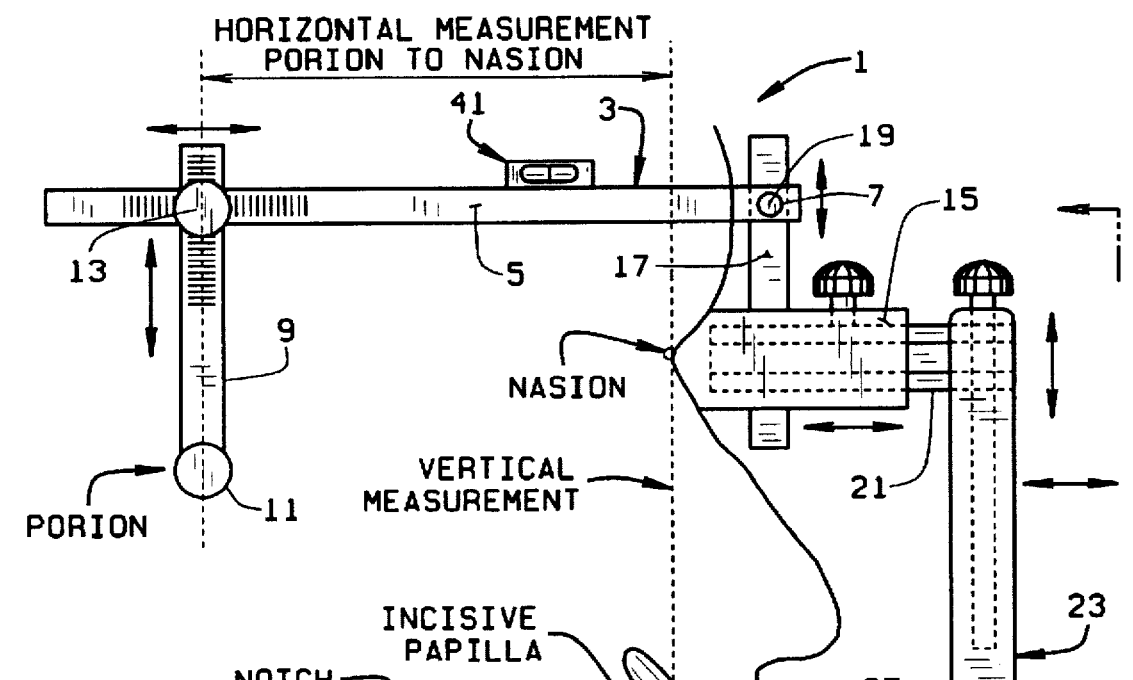
FIG. 1 is a side elevational view of a patient's head illustrating key anatomical and dental features of the patient with the patient having a radiographic evaluation apparatus of the present invention installed on the patient's head with a bite fork inserted in the patient's mouth.
Figure 2:
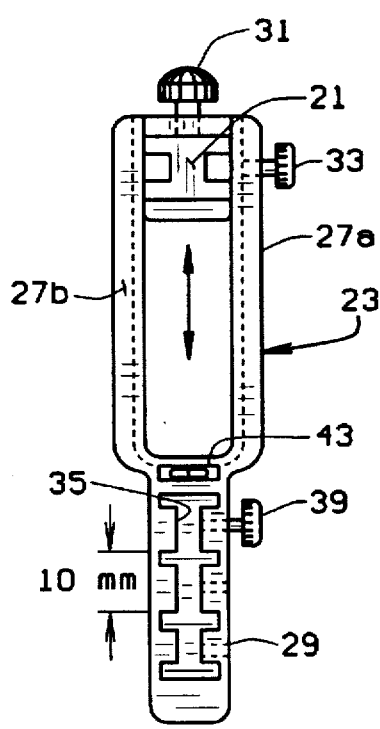
FIG. 2 is a from elevational view of a bite wing support member carded by the face bow shown in FIG. 1.
Figure 3:
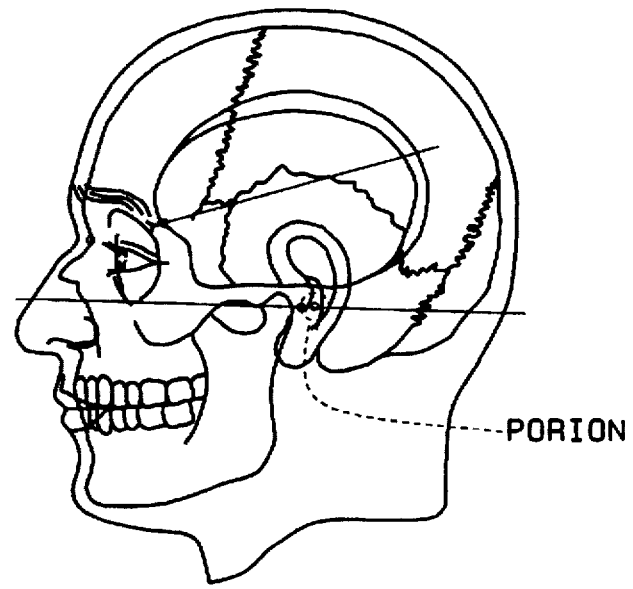
FIG. 3 is an anatomical diagram illustrating key anatomical and skeletal reference points of the cranial bones.

Referring now to the drawings, and more particularly to FIGS. 1–3. apparatus of the present invention, as is generally indicated in its entirety by reference character 1, is illustrated which orients the patient's head in a true horizontal plane. This apparatus comprises a head holder or face bow 3 having temple pieces 5 positioned at each side of the head and extending from a position above and to the rear of the patient's ear forwardly in front of the patient's forehead. The face bow includes a front portion 7 which extends laterally across the front of the patient's head above the orbits of the eyes. The face bow includes a pair of ear pieces, as indicated at 9, which extend downwardly from the rearward end portions of temple pieces 5. Each of the ear pieces has an ear finger 11 which projects into and is engageable with the patient's porion or ear opening. As indicated at 13, an adjustable connection is provided between each of the temple pieces 5 and its respective ear piece 9 for both vertical and horizontal adjustment of the temples and ear pieces relative to one another. As will be appreciated, the adjustable connection 13 includes an adjustment screw which may be tightened to lock the ear piece to its temple piece in a desired vertical and horizontal position and which may be loosened to facilitate adjustment between the ear piece and its respective temple piece.

Extending downwardly from the front portion 7 of face bow 3 is a nose piece, as generally indicated at 15. This nose piece is carried by a nose piece support rod 17 which extends downwardly from the front portion 7 of the face bow and which is connected thereto by means of an adjustment screw connection 19 which when tightened securely locks the nose piece support rod 17 relative to the front portion 7 of the face bow in a desired vertical position relative to the face bow. Nose piece 15 has an end portion which is adapted to be engageable with the nasion of the patient's nose structure, generally shown in FIG. 1.

A so-called mounting key or beam 21 extends in horizontal direction from nose piece 15 away from the patient's nose and carries a generally vertically disposed bite fork support member 23. The bite fork support member carries a bite fork 25 which is adapted to be inserted into the patient's mouth, as generally shown in FIG. 1, with the bite fork being supported in a generally horizontal position. As best shown in FIG. 2, bite fork support member 23 generally a Y-shaped member having a pair of spaced apart arms 27a, 27b, and having a tail portion 29 extending downwardly therefrom. The space between arms 27a, 27b is such as to receive mounting key 21 there between. As shown best in FIG. 2, mounting key 21 is generally of I-shaped cross section. An adjustment screw 31 is carded by the upper portion of the bite fork support for engaging the upper surface of the mounting key thereby to hold the bite fork support member in fixed axial position along the length of the mounting key. A vertical slot is provided and adjustment screw 33 is carried by the mounting key 21 and extends through the vertical slot in arm 27a such that the bite support member may be moved up and down relative to mounting key 21 and locked in place by means of the adjustment screw 33.

Three Siamese I-shaped slots 35 are provided in tail 29 for receiving the I-shaped extension 37 of bite fork 25. An adjustment screw 39 is provided for locking the extension 37 in fixed horizontal position with respect to tail 29 of bite fork support 23. In this manner, the bite fork may be adjusted in and out of the patient's mouth in a generally horizontal direction and locked in a desired position horizontal an engaged with one or more desired teeth.

In accordance with this invention, a bubble level 41 is carried by one or both temple piece(s) 5 and the anterior face bow piece of face bow 3 so as to indicate when the portion of the face bow 3 carrying bubble level 41 is in a level, horizontal position. It will be understood that the adjustable connection 13 between ear piece 9 and the temple member 5 and the adjustable connection 19 between the front portion 7 of face bow 3 and nose piece 15 can be adjusted such that with ear (holders or supports) fingers 11 properly inserted in the patient's potions or ear openings and with the end of nose piece 15 properly engaging the patient's nasion, bubble level(s) 41 enable the practitioner to adjust the portions of face bow 3 carrying level(s) 41 to in a true horizontal plane. Further in accordance with this invention, a second bubble level, as generally indicated at 43, is carded by bite fork support 23 so as to indicate when the bite fork support member is in a true vertical position. It will be appreciated that bite fork support 23 is perpendicular to mounting key 21 which in turn is perpendicular to nose piece support rod 17 and which in turn is perpendicular to the forward part 7 of face bow 3. Of course, the forward portion of the face bow has been previously adjusted to be in a true horizontal position, as determined by bubble level(s) 41, such that bite fork 25 is substantially horizontal within the patient's mouth.

In use, cephalometric apparatus 1 of the present invention is installed on the patient's head, generally as shown in FIG. 1 with the ear pieces 9 inserted into the patient's potions and with the end of nose piece 15 engaging the patient's nasion. Then, temple piece(s) 5 are adjusted relative to ear pieces 9 and support piece 17 is adjusted relative to the front portion 7 of face bow 3 such that the temple piece(s) 5 are established to be in a true horizontal plane, as determined by bubble level(s) 41. Simultaneously, bite wing support member 23 is adjusted both vertically and horizontally so as to position bite fork 25 in a generally horizontal position within the patient's mouth and relative to the patient's upper teeth. With the face bow in its true horizontal position, bite fork support 23 is adjusted to be in a true vertical plane, as established by bubble level 43. With the patient's head so positioned and with respect to a true horizontal reference plane as established by level(s) 41, photographs and radiographic images of the patient's features can then be taken. If desired, bite fork 25 can be utilized to take impressions of the biting or occlusal surfaces of the patient's upper dentition. The bite registration can then be used by the practitioner to repeatedly mount the patient's study cast to a true horizontal and reference plane. It will be further appreciated that the use of the evaluation methods disclosed above are important because they utilize the same horizontal and vertical reference planes in a manner which is reproducible and consistent from practitioner to practitioner and which is consistent for the same practitioner each time such cephalometric measurements are taken for the patent. This provides a greater accuracy than existing cephalometric methods and allows diagnostic procedures to be referenced to the same horizontal and vertical orientation planes.

It will be appreciated that within the broader scope of this invention, it is highly beneficial to accurately establish the patient's head in a desired horizontal and vertical reference plane. To do this, it is not necessary to utilize the bite fork 25 or the bite fork support member, but rather it is only necessary to use face bow 3, temple pieces 5, and ear pieces 9 in conjunction with the horizontal bubble level(s) 41.

In view of the above, it will be seen that the several objects and features of this invention are achieved and that other advantageous results are attained.

As various changes could be made in the above constructions and methods without departing from the scope of the invention, it is intended that all matter contained in the above description are shown in the accompanying drawings shall be interpreted as illustrative and not in a limiting sense.

What is claimed is:

1. An cephalometric evaluation reference determining apparatus for use on a dental patient comprising a face bow adapted to extend generally from one of the patient's ears forwardly along the patient's temples, across the front of the patient's head, and along the other side of the patient's head along the temple to the patient's other ear, a pair of ear pieces adjustably connected to said face bow, each said ear piece being adapted to be inserted into a respective one of the patient's ear openings, a nose piece adjustably carried by the portion of said face bow extending across the front of the patient's face, said nose piece having a portion thereof adapted to engage the patient's nasion, and a level for reproducibly establishing the position of the patient's ear openings and nasion relative to a true horizontal reference plane.

2. A cephalometric reference determining apparatus as said forth in claim 1 wherein said adjustable connection between said ear piece and said face bow permits both vertical and horizontal adjustment between said ear piece and said face bow and a securement for locking said ear piece and said face bow in a desired vertical and horizontal position relative to one another.

3. A cephalometric reference determining apparatus as said forth in claim 1 further comprising a nose piece support carried by the front portion of said face bow, said nose piece being carried by said nose support piece and being adjustable relative to said face bow in vertical direction and being adjustable relative to said nose piece support in horizontal direction so as to engage the patient's nasion.

4. A cephalometric reference determining apparatus as said forth in claim 3 further comprising a non-rotating horizontal support member extending endwise from said nose piece, and a generally vertically disposed bite wing support extending downwardly from said horizontal support member, said vertical support carrying a non-rotating bite wing for insertion in generally horizontal direction into the patient's mouth.

5. A cephalometric reference determining apparatus as said forth in claim 4 further comprising a level determining means carried by said bite fork support member for establishing said bite fork support member in a true vertical plane.

6. A method of determining a true horizontal reference for the head of a dental patient comprising the steps of placing a face bow on the patient's head, said face bow comprising temple pieces extending from one of the patient's ears forwardly along the patient's temples, a front portion extending laterally across the patient's forehead, an ear piece extending down from each of the temple pieces and a nose piece extending down from said front portion, said method further comprising positioning an ear finger carded by each of said ear pieces within the patient's potions or ear openings, positioning said nose piece so as to engage the patient's nasion, and adjusting the ear pieces and the nose piece relative to at least a portion of the temple pieces such that such portion of the temple pieces are in a true horizontal position as established by a level.

7. A cephalometric reference apparatus for use on a dental patient comprising:

- a face bow adapted to traverse the upper portion of the patient's face, said face bow having a first terminus above one of the patient's ears, extending forwardly to a frontal portion crossing the patient's face, and back to a second terminus above the patient's other ear;
- an ear piece adjustably secured to said face bow adjacent each terminus, each of said ear pieces comprising ear finger portions adapted for insertion within the patient's ear openings;
- a nose piece adjustably secured to said frontal portion of said face bow, said nose piece adapted to engage the patient's nasion; and
- a plurality of levels mounted on said face bow for reproducibly establishing true horizontal and vertical reference planes relative to said face bow.

8. A cephalometric reference apparatus for use on a dental patient, comprising:

- a face bow adapted for removably securing to the patient's head; and
- a first and second level mounted on said face bow, said first and second levels adapted for establishing said face bow and the patient's head in a predetermined position relative to true horizontal and vertical planes.

9. A cephalometric reference apparatus for use on a dental patient comprising:

- a face bow adapted to extend around the patient's head, said face bow comprising temple pieces extending from one of the patient's ears forwardly along the patient's temples, a front portion extending laterally across the patient's forehead;
- ear pieces adjustably secured to extend down from each of said temple pieces, said ear pieces comprising ear fingers adapted for insertion the patient's porions;
- a nose piece adjustably extending down from said front portion, said nose piece adapted for engaging the patient's nasion; and
- a first and second level secured to said face bow, said first and second levels adapted to reproducibly establish said face bow and patient's head in true horizontal and vertical planes.

* * * * *

UNITED STATES PATENT AND TRADEMARK OFFICE
CERTIFICATE OF CORRECTION

PATENT NO. : 5,738,517
DATED : April 14, 1998
INVENTOR(S) : Duane C. Keller

It is certified that error appears in the above-identified patent and that said Letters Patent is hereby corrected as shown below:

Col. 1, line 58
 replace "reproducible"
 with --reproducible,--.

Col. 1, line 58
 replace "plane"
 with --plane,--.

Col. 2, line 29
 replace "potions"
 with --porions--.

Col. 2, line 33
 replace "carded"
 with --carried--.

Col. 2, line 47
 replace "potions"
 with --porions--.

Col. 2, line 62
 replace "from"
 with --front--.

Col. 3, line 51
 replace "carded"
 with --carried--.

column 3, line 66 and column 4, line 13
 "an" should read --and--; and Delete "in".

Signed and Sealed this

Twenty-second Day of December, 1998

*Attest:*

BRUCE LEHMAN

*Attesting Officer*    *Commissioner of Patents and Trademarks*